United States Patent [19]

Wagner et al.

[11] Patent Number: 5,618,975

[45] Date of Patent: Apr. 8, 1997

[54] PROCESS FOR THE PREPARATION OF BIPHENYL DERIVATIVES

[75] Inventors: Adalbert Wagner, Hattersheim/Main, Germany; Neerja Bhatnagar, Savigny Sur Orge, France; Jean Buendia, Le Perreux Sur Marne, France; Christine Griffoul, Rosny Sous Bois, France

[73] Assignee: Hoechst Aktiengesellschaft, Frankfurt am Main, Germany

[21] Appl. No.: 449,396

[22] Filed: May 24, 1995

Related U.S. Application Data

[62] Division of Ser. No. 177,314, Jan. 4, 1994, abandoned.

[30] Foreign Application Priority Data

Jan. 6, 1993 [DE] Germany .................. 43 00 137.8

[51] Int. Cl.⁶ ..................... C07C 311/21; C07C 47/546
[52] U.S. Cl. ................... 564/88; 548/253; 564/99; 568/31; 568/425
[58] Field of Search ............... 564/99, 88; 548/253; 568/425, 31; 514/602, 621

[56] References Cited

U.S. PATENT DOCUMENTS

| | | | |
|---|---|---|---|
| 3,624,142 | 11/1971 | Shen et al. ................. | 568/31 X |
| 3,950,427 | 4/1976 | Engel et al. . | |
| 5,068,424 | 11/1991 | Besenyei et al. . | |
| 5,130,439 | 7/1992 | Lo et al. . | |

FOREIGN PATENT DOCUMENTS

| | | |
|---|---|---|
| 2027839 | 4/1991 | Canada . |
| 2038428 | 9/1991 | Canada . |
| 2058198 | 7/1992 | Canada . |
| 2086364 | 7/1993 | Canada . |
| 0424317A3 | 4/1991 | European Pat. Off. . |
| 0449699A2 | 10/1991 | European Pat. Off. . |
| 0499415A1 | 8/1992 | European Pat. Off. . |
| 0503162A1 | 9/1992 | European Pat. Off. . |
| 0550313A1 | 7/1993 | European Pat. Off. . |
| 2632952 | 12/1989 | France . |
| 2362589 | 7/1975 | Germany . |

OTHER PUBLICATIONS

Hegedus et al., Organometallics 1984, vol. 3, pp. 1263–1267.
Miyura et al., Synthetic Communications, vol. 11, No. 7, pp. 513–519, 1981.
Feulner et al., Chem. Ber., vol. 123, pp. 1841–1843, 1990.
Sabatka et al., Journal of Chromatography, vol. 384, pp. 349–356, 1987.
Glover et al., Journal of the Chemical Society, Perkin Transactions I, vol. 6, pp. 653–657, 1978.
Bradbury et al., J. Med. Chem, vol. 35, pp. 4027–4038, 1992.
Atwal et al., J. Med. Chem. vol. 35, pp. 4751–4763, 1992.
Miller et al., Organometallics, vol. 3, pp. 1261–1263, 1984.
Miyaura et al., Synthetic Communications, vol. 11, No. 7, pp. 513–519, 1981.

Watanabe et al., "Synthesis of Sterically Hindered Biaryls via the Palladium–Catalyzed Cross–Coupling Reaction of Arylboronic Acids or their Esters with Haloarenes," Synlett, Mar. 1992, pp. 207–210.

*Primary Examiner*—Richard D. Lovering
*Attorney, Agent, or Firm*—Finnegan, Henderson, Farabow, Garrett & Dunner, L.L.P.

[57] ABSTRACT

Biphenyl derivatives and processes for the preparation of biphenyl derivatives are described. A compound of formula (I) is disclosed

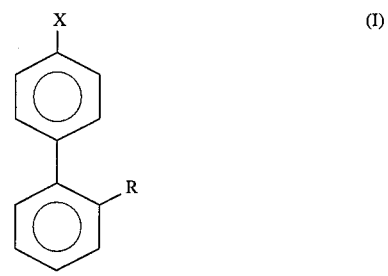

in which the substituent X is —CHO or —CH(OR¹)OR², where R¹ and R² independently of one another are (C₁–C₆)-alkyl or R¹ and R² together are an alkylene group (—CH₂)ₙ—, where n is 2, 3 4 or 5 and R is —F, —Cl, —NO₂, —(CH₂)ₘ—COOR³, —(CH₂)ₘ—CONHR³, —(CH₂)ₘ—CN, —SO₂NH—COOR³, —SO₂NH—CO—NHR³, —SO₂NH—SO₂—R³, —NHSO₂R³,

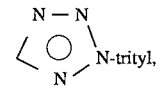

—PO₃R³, —NH—SO₂—CF₃, —SO₂NR⁴
where R³ is hydrogen, (C₁–C₆)-alkyl, (C₃–C₆)cycloalkyl, or (C₁–C₆)-alkyl-(C₃–C₆)cycloalkyl and R⁴ is a group =C—N(CH₃)₂, and m is 0, 1, 2, 3, or 4. The invention also relates to a process for the preparation of a compound of the formula (I) in which X is an optionally protected formyl group and R is a group which is itself inert to the reaction conditions of the synthesis, which comprises reacting a compound of the formula (II)

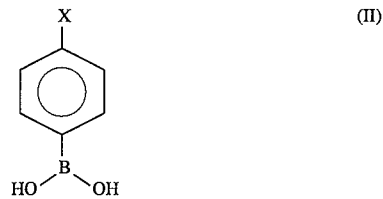

with a substituted phenyl-halogen compound of the formula (III)

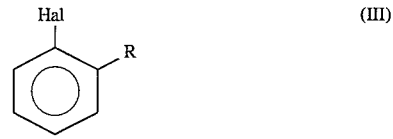

wherein the substituent Hal is a halogen group.

14 Claims, No Drawings

PROCESS FOR THE PREPARATION OF BIPHENYL DERIVATIVES

This is a division of application Ser. No. 08/177,314, filed Jan. 4, 1994, abandoned.

The invention relates to specific biphenyl derivatives and to a process for their preparation.

In the preparation of active substances such as, for example, pharmaceuticals for cardiovascular disorders, biphenyl derivatives have turned out to be important intermediates in the preparation process. For example, in EP-A 503 162 the preparation of hypotensive preparations is described which contain, as the active substance, compounds of the angiotensin II receptor antagonist type which have a specifically substituted biphenyl system.

Various preparation processes for substituted biphenyl derivatives have already been described, for example phenylboronic acid derivatives can be coupled with aryl halides using transition metal catalysts, for example palladium. Corresponding reactions have been described by R. B. Miller et al. in Organometallics 1984, 3, 1261 or by A. Zuzuki et al. in Synthetic Commun. 11(7), 513 (1981).

The invention relates to a process for the preparation of biphenyl derivatives of the formula (I)

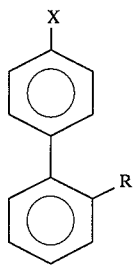

in which

X is an optionally protected formyl group, in particular —CHO or —CH(OR$^1$)OR$^2$, R$^1$ and R$^2$ independently of one another are (C$_1$–C$_6$)-alkyl or R$^1$ and R$^2$ together are an alkylene group —(CH$_2$)$_n$—, where n is 2, 3, 4 or 5, and R is a group which is itself inert to the reaction conditions of the synthesis.

In the process according to the invention, starting from known, optionally protected formylbenzene halides, for example the bromides or iodides, boronic acid derivatives of the formula (II) are prepared via a Grignard reaction (see e.g. H. Feulher et al.; Chemische Berichte 123 (1990) 1841–1843),

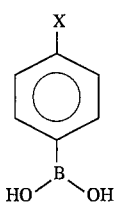

the group X in formula (II) being a CHO group or an appropriately protected formyl group, for example an acetal. The compounds of the formula (II) are then converted by coupling with substituted phenylhalogen compounds of the formula (III)

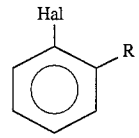

which can be obtained by known methods, to give the biphenyl compounds of the formula (I), suitable halogen groups (Hal) for the compounds of the formula (III) preferred being the bromides and iodides, particularly preferred being the bromides, and R being as defined above.

Instead of the boronic acid derivatives of the formula (II), esters of the respective boronic acids can be used in the process according to the invention which for example can be prepared from the respective bromo methyl benzene boronic acid derivatives.

The linking of the two phenyl derivatives of the formulae (II) and (III) to give the corresponding biphenyl compound can be carried out using a catalyst preferably a palladiuan catalyst. The reaction conditions can be varied depending on the reactivity of the starting substances, a temperature range from about 20° C. to 150° C. and a pressure from 1 bar to 5 bar is preferably used. Suitable solvents are e.g. mixtures of benzene or toluene with alcohols, in particular ethanol.

Suitable substituents R in the compounds of the formula (I) are all groups which are not themselves modified under the reaction conditions used for the linkage of the two phenyl rings. The following groups are particularly suitable as substituents R:

R is —F, —Cl, —NO$_2$, —(CH$_2$)$_m$—COOR$^3$, —(CH$_2$)$_m$—CONHR$^3$, —(CH$_2$)$_m$—CN, —SO$_2$NH—COOR$^3$, —SO$_2$NH—CO—NHR$^3$, —SO$_2$NH—SO$_2$—R$^3$, —NHSO$_2$R$^3$,

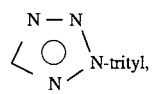

—PO$_3$R$^3$, —NH—SO$_2$—CF$_3$ or —SO$_2$NR$^4$ where R$^3$ is hydrogen, (C$_1$–C$_6$)-alkyl, (C$_3$–C$_6$)cycloalkyl or (C$_1$–C$_6$)-alkyl-(C$_3$–C$_6$) cycloalkyl and R$^4$ is a group =C—N(CH$_3$)$_2$, and m is 0, 1, 2, 3 or 4.

Instead of linkage of the two phenyl systems via a boronic acid derivative, the preparation of the biphenyl derivatives of the formula (I) can also be carried out using zinc halide phenyl derivatives, methyltin phenyl derivatives or Grignard compounds.

The protected formyl group and the Grignard reagents are prepared by customary methods.

The invention also relates to the compounds of the formula (I) as such, compounds being preferred in which R is SO$_2$NHCOOR$^3$, SO$_2$NHCONHR$^3$, SO$_2$NHSO$_2$R$^3$ or SO$_2$NR$^4$, SO$_2$NHCONHR$^3$ and SO$_2$NR$^4$ being particularly preferred, and to the compounds of the formula (III) as such, compounds being preferred in which R is —SO$_2$NH—COOR$^3$, —SO$_2$NH—CO—NHR$^3$ or SO$_2$NH—SO$_2$—R$^3$, SO$_2$NH—CO—NHR$^3$ being particularly preferred.

The invention is illustrated in greater detail by the following examples.

EXAMPLE 1

Process for the preparation of 4-formyl-2'-N,N-dimethylaminoformylbiphenylsulfonamide

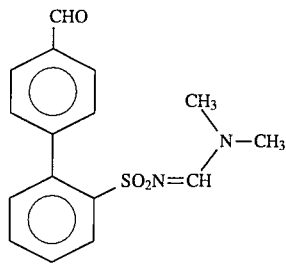

1a) 4-Bromobenzaldehyde diethyl acetal 100 g (0.54 tool) of molten 4-bromobenzaldehyde and 90 ml (0.54 tool) of triethyl orthoformate are added to 2.7 g of ammonium nitrate in 65 ml (1.1 mol) of anhydrous ethanol. After 18 hours at room temperature, solid is filtered off and the filtrate is rendered alkaline using piperidine (~pH 10). The title compound is obtained by distillation in vacuo.

Yield: 90% Boiling point: (at 0.05 mm HG)=110°–115° C.

1b) 4-Formylbenzeneboronic acid

Under an argon atmosphere, 3.65 g of magnesium turnings are covered with 15 ml of anhydrous THF and treated with 0.5 ml of 1,2-dibromoethane. Gentle warming leads to a vigorous reaction. After the reaction has subsided, the solvent is pipetted off with a pipette, treated with 40 ml of anhydrous THF and ⅓ of a solution of 32 g of the product 1a) in 30 ml of anhydrous THF are added. The reaction is started with Red-A1 and by warming. The remainder of the product from 1a) is then added dropwise within the course of 35 min. After dropwise addition is complete, the mixture is boiled under reflux for a further 1 h. The Grignard product is then added dropwise to a solution, cooled to −68° C., of 33.5 ml of tributyl borate under an argon atmosphere in 50 ml of THF. After 30 min, the cooling is removed. The mixture is then stirred at RT for 1 h. It is then concentrated, the honey-colored oil is taken up in 100 ml of ether and 80 ml of ice-cold $H_2SO_4$ (1M) are added. The ether phase is separated off and extracted twice more with 50 ml of ether, concentrated and 30% strength (6N) KOH is added until an alkaline reaction (pH 14) occurs. 70ml of $H_2O$ are added and the butanol is removed azeotropically at 35°–40° C. in a high vacuum. This process is repeated again with 50 ml of $H_2O$. The residue is rendered acidic with 1M $H_2SO_4$ (pH 1) and boiled for 30 min. The title compound is obtained as a pale yellow solid by filtration.

m.p.=255°–60° C.

1c) 4-Formyl-2'-N,N-dimethylaminoformylbiphenylsulfonamide 5.7 g of sodium carbonate (2 equivalents) in 30 ml of $H_2O$ are added warm to 7 g (0.024 mol) of 2-bromo-N,N-dimethylaminoformylbenzenesulfonamide and 0.7 g of triphenylphosphine (0.1 equivalent) in 100 ml of toluene. The mixture is flushed well with argon and 0.3 g of palladium acetate (0.05 equivalent) are added in an argon countercurrent at 60° C. After 10 minutes, 4 g of the compound from 1b ) (1.1 equivalents) in 70 ml of ethanol are added in the argon countercurrent to the meanwhile very dark brown reaction solution. The mixture is then heated to boiling point and boiled under reflux for 3½ hours. After cooling, the solvent is removed in vacuo. The residue is taken up in 150 ml of ethyl acetate and washed 5× with saturated sodium carbonate solution. The organic phase is dried using magnesium sulfate and filtered through a layer of celite. After removal of the solvent in vacuo, 8 g of the title compound are obtained as brown, partially crystalline crude substance. This can be purified by boiling up in about 30 ml of ethyl acetate.

Yield: 83% $R_f$=0.4 (E/H 2/1); MS (M+1)=317
M.p.: 161° C.

The compounds of Examples 2 to 6 are prepared analogously starting from appropriate starting materials. These compounds are shown in Table 1 with structure and physical data.

TABLE 1

| Example No. | R | MS (M + 1) |
|---|---|---|
| 2 | $-CO_2C_2H_5$ | 255 |
| 3 | $-CN$ | 208 |
| 4 | (tetrazole, N-Trityl) | 493 |
| 5 | $-SO_2NHCONHC_3H_7$ | 347 |
| 6 | $-NHSO_2CF_3$ | 330 |

Examples 7 and 8 describe the preparation of intermediate compounds of formula (III)

EXAMPLE 7

Preparation of 2-bromobenzene-n-propylsulfonylurea 3.5 g (15 mmol) of 2-bromobenzenesulfonamide and 4.1 g $K_2CO_3$ are refluxed in dimethoxypropane for 1 hour. After that time 3 ml of n-propyliocyanate are added via a syringe. After additional 12 hours, the solution is cooled to 0° C., the pH is adjusted to 5–6 using 5% $NaHSO_4$ and this mixture is extracted twice with ethyl acetate. The combined organic extracts are dried over $MgSO_4$ and the solvent is removed. Cristallization from ethyl acetate furnishes the title compound. $R_f$=0.5 (E/H 2/1); MS (M+1)=321

EXAMPLE 8

Process for the preparation of 2-iodobenzene-n-propylsulfonylurea a) 2-iodobenzene sulfonamide 2-aminobenzene sulfonamide (3.5 g) in conc. $H_2SO_4$, 98% (25 ml) are heated at 60° to give a clear solution. 20 g of ice is then added and the solution is cooled to 0° C. $NaNO_2$ (1.45 g) in water (4 ml) is added dropwise very carefully without exceeding 5°–6° C. The reaction mixture is stirred at 5°–6° C. for 3 hours. A solution of potassium iodide (3.75 g) in $H_2O$ (25 ml) is then introduced dropwise and the obtained red mixture is stirred for 18 hours. $H_2O$ (50 ml) is added and the obtained precipitate is filtered, washed several times in water. The obtained solid is dissolved in ethyl acetate, washed once with 0.2N sodiumthiosulfate solution and twice with water, evaporated to dryness to give 4 g of a light yellow compound (62% yield).

m.p.=197°198° C., IR (nujol): 3360, 3255, 1562 cm$^{-1}$, MS (M$^+$):283

8b) 2-iodobenzene-n-propylsulfonylurea

To a stirred solution of 2-iodo benzene sulfonamide (4 g) in acetone (40 ml) solid K$_2$CO$_3$ (3.92 g) is added in one portion and the mixture is refluxed under N$_2$-atmosphere, n-propyl isocyanate is added dropwise to the heated mixture. After 2 hours reflux, the reaction is cooled to room temperature and concentrated to dryness. Water (200 ml) is added and the cooled mixture is acidified with 2N HCl to pH 4 and filtered. The precipitate obtained is recristallised with acetone/isopropyl ether mixture to give 4.1 g solid of the title compound.

m.p.=211°–212° C.; IR (nujol): 3368, 1715, 1565, 1539 cm$^{-1}$; MS (M$^+$):368

Table 2 summarizes the $^1$H-NMR-data (200 MHz) for the title compounds of examples 1, 2, 3, 5, 8a and 8b.

Table 2:

1: (DMSO-d$_6$) d=2.68 (s, 3H); d=2.72 (s, 3H); d =7.2 (s, 1H); d=7.25 to 7.35 (m, 1H); d=7.45 to 7.75 (m, 4H); d=7.95 (d, J=8 Hz, 1H); d=8.05 to 8.15 (m, 2H); d=10.1 (s, 1H).

2: (CDCl$_3$) d=1.0 (t, J=7 Hz, 3 H; d=4.1 (q, J=7 Hz, 2H); d=7.3 to 7.6 (m, 5H); d=7.85 to 8.0 (m, 3H); d=10.1 (s, 1H).

3: (CDCl$_3$) d=7.2 to 7.8 (m, 6H); 7.95 to 8.05 (m, 2H); d=10.1 (s, 1H).

5: (DMSO-d$_6$) d=1.0 (t, J=7 Hz, 3H); d=1.3 (dq, J=7 Hz, 2H); d=2.85 (dd, J=7 Hz, J=9.5 Hz, 2H); d=6.1 (t, J=7 Hz, 1H); d=7.1 to 7.4 (m, 1H); d=7.4 to 7.8 (m, 4H); d=7.9 to 8.1 (m, 3H); d=9.9 (s, 1H); d=10.1 (s, 1H).

8a. (CDCl$_3$) 5.17 (s, 1, NH$_2$); 7.23 to 7.52 (td aromatics 2H); 8.08 to 8.20 (dd, aromatics 2H)

8b: (CDCl$_3$) 0.82 (t, J=7.5CH$_3$, 3H); 1.45 (m, CH$_2$, 2 H; 3.14 (m, CH$_2$, 2H); 6.39 (t, CONH, 1H); 7.29 (dt, J=1.5 aromatics); 7,54 (td, J=8.15 aromatics); 8.13 (m, aromatics) 7.59 (s, SO$_2$NH, 1H).

Abbreviations:

E Ethyl acetate

H n-Heptane

Red-Al Sodium dihydridobis-(2-methoxyethoxy)aluminate

THF Tetrahydrofuran

Trityl Triphenylmethyl

We claim:

1. A compound of the formula (I)

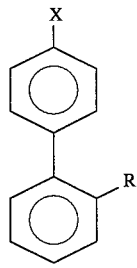

(I)

in which the substituents have the following meanings,

X is —CHO or —CH(OR$^1$)OR$^2$, where

R$^1$ and R$^2$ independently of one another are (C$_1$–C$_6$)-alkyl or R$^1$ and R$^2$ together are an alkylene group (—CH$_2$)$_n$—, where n is 2, 3, 4, or 5, and R is —(CH$_2$)$_m$—COOR$^3$, —(CH$_2$)$_m$—CONHR$^3$, —(CH$_2$)$_m$—CN, —SO$_2$NH—COOR$^3$, —SO$_2$NH—CO—NHR$^3$, —SO$_2$NH—SO$_2$—R$^3$,

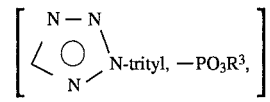

—NHSO$_2$R$^3$, —NH—SO$_2$—CF$_3$, or —SO$_2$NR$^4$ where R$^3$ is hydrogen, (C$_1$—C$_6$)-alkyl, (C$_3$—C$_6$)cycloalkyl, or (C$_1$–C$_6$)-alkyl-(C$_3$–C$_6$)cycloalkyl and R$^4$ is a group =C—N(CH$_3$)$_2$, and m is 1, 2, 3, or 4.

2. A compound as claimed in claim 1, wherein formula (I) R is SO$_2$—NR$^4$ or SO$_2$NHCONHR$^3$, where R$^3$ is hydrogen or C$_1$-C$_6$-alkyl and R$^4$ is a group =C—N (CH$_3$)$_2$.

3. A compound as claimed in claim 1, wherein in formula (I), R is —SO$_2$NH—SO$_2$—R$^3$, wherein R$^3$ is hydrogen, (C$_1$–C$_6$)-alkyl, (C$_3$–C$_6$)-cycloalkyl, or (C$_1$–C$_6$)-alkyl-(C$_3$–C$_6$)-cycloalkyl.

4. The compound of claim 3, wherein X is —CHO.

5. A compound as claimed in claim 1, wherein in formula (I) , R is —SO$_2$NR$^4$ wherein R$^4$ is a group =C—N (CH$_3$)$_2$.

6. The compound of claim 5, wherein X is —CHO.

7. A compound as claimed in claim 1, wherein in formula (I), R is —SO$_2$NH—CO—NHR$^3$, wherein R$^3$ is hydrogen, (C$_1$–C$_6$)-alkyl, (C$_3$–C$_6$)-cycloalkyl, or (C$_1$–C$_6$)-alkyl-(C$_3$–C$_6$)-cycloalkyl.

8. The compound of claim 7, wherein X is —CHO.

9. A compound as claimed in claim 1, wherein in formula (I), R is —SO$_2$NH—COOR$^3$, wherein R$^3$ is hydrogen, (C$_1$–C$_6$)-alkyl, (C$_3$–C$_6$)-cycloalkyl, or (C$_1$–C$_6$)-alkyl-(C$_3$–C$_6$)-cycloalkyl.

10. The compound of claim 9, wherein X is —CHO.

11. A compound as claimed in claim 1, wherein in formula (I), R is —NHSO$_2$R$^3$, wherein R$^3$ is hydrogen (C$_1$–C$_6$)-alkyl, (C$_3$–C$_6$)-cycloalkyl, or (C$_1$–C$_6$)-alkyl-(C$_3$–C$_6$)-cycloalkyl.

12. The compound of claim 11, wherein X is —CHO.

13. A compound as claimed in claim 1, wherein in formula (I), R is —NH—SO$_2$—CF$_3$.

14. The compound of claim 13, wherein X is —CHO.

* * * * *

UNITED STATES PATENT AND TRADEMARK OFFICE
CERTIFICATE OF CORRECTION

PATENT NO. : 5,618,975
DATED : April 8, 1997
INVENTOR(S) : Adalbert WAGNER et al.

It is certified that error appears in the above-indentified patent and that said Letters Patent is hereby corrected as shown below:

On the Title page, Item [57],
in the Abstract, line 8, after "5" insert --,--.

Claim 1, column 6, lines 11-15, delete
" 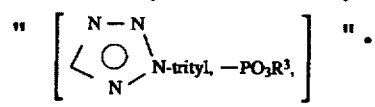 ".

Claim 5, column 6, line 35, after "-SO$_2$NR$^4$", insert --,--.

Claim 11, column 6, line 51, after "hydrogen" insert --,--.

Signed and Sealed this

Twenty-third Day of September, 1997

*Attest:*

BRUCE LEHMAN

*Attesting Officer*     Commissioner of Patents and Trademarks